(12) United States Patent
Bhat

(10) Patent No.: US 6,706,034 B1
(45) Date of Patent: Mar. 16, 2004

(54) PROCESS FOR AGENT RETENTION IN BIOLOGICAL TISSUES

(75) Inventor: Vinayak D. Bhat, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/475,649

(22) Filed: Dec. 30, 1999

(51) Int. Cl.[7] .................. A61K 9/22; A61K 9/14; A61F 2/06; A61F 2/28
(52) U.S. Cl. ............ 604/890.1; 623/1.42; 623/23.59; 424/484
(58) Field of Search ............ 604/890.1, 891.1; 623/11.11, 23.59, 1.42; 424/450, 484, 490; 427/2.24, 2.31

(56) References Cited

U.S. PATENT DOCUMENTS

| | | | |
|---|---|---|---|
| 3,910,862 A | * | 10/1975 | Barabas et al. ............ 260/79.3 |
| 4,617,186 A | | 10/1986 | Schafer et al. |
| 4,852,568 A | * | 8/1989 | Kensey ............ 128/325 |
| 5,149,543 A | | 9/1992 | Cohen et al. |
| 5,294,314 A | * | 3/1994 | Nesburn et al. ....... 204/157.68 |
| 5,308,701 A | | 5/1994 | Cohen et al. |
| 5,380,307 A | | 1/1995 | Chee et al. |
| 5,462,523 A | | 10/1995 | Samson et al. |
| 5,494,682 A | | 2/1996 | Cohen et al. |
| 5,538,504 A | | 7/1996 | Linden et al. |
| 5,575,815 A | * | 11/1996 | Slepian et al. ............ 623/1 |
| 5,588,962 A | | 12/1996 | Nicholas et al. |
| 5,674,192 A | * | 10/1997 | Sahatjian et al. ............ 604/28 |
| 5,726,144 A | * | 3/1998 | Dewez et al. ............ 510/522 |
| 5,733,868 A | * | 3/1998 | Peterson et al. ............ 514/2 |
| 5,749,915 A | | 5/1998 | Slepian |
| 5,749,922 A | | 5/1998 | Slepian et al. |
| 5,795,318 A | | 8/1998 | Wang et al. |
| 5,797,870 A | | 8/1998 | March et al. |
| 5,866,561 A | | 2/1999 | Ungs |
| 6,228,845 B1 | * | 5/2001 | Donovan et al. ............ 514/44 |
| 6,395,029 B1 | * | 5/2002 | Levy ............ 623/11.11 |

FOREIGN PATENT DOCUMENTS

WO    WO 99/03484    1/1999

OTHER PUBLICATIONS

R. Riessen et al., "Prospects for Site Specific Delivery of Pharmacological and Molecular Therapies," J. Am. Col. Card., Apr. 1994, pp. 1234–1244, vol 23:5.

Y. Akamo, et al., "Chemotherapy Targeting Regional Lymph Nodes By Gastric Submucosal Injection of Liposomal Adriamycin in Patients With Gastric Carcinoma," Jpn. J. Cancer Research, Jun. 1994, pp. 652–658, vol. 85:6.

E. Nabel, et al., "Safety and Toxicity of Catheter Gene Delivery to the Pulmonary Vasculature in a Patient With Metastatic Melanoma," Hum. Gene. Ther., Sep. 1994, pp. 1089–1094, vol. 5:9, Mary Ann Liebert.

B. Ratner, et al., Biomaterials Science: Introduction to Materials and Medicine, 1996, pp. 68–69, Academic Press.

I. Raad, et al., "Silver Iontophoretic Catheter: A Prototype of a Long–Term Antiinfective Vascular Access Device," J. Infect. Dis., Feb. 1996, pp. 495–498, vol. 173:2.

(List continued on next page.)

*Primary Examiner*—Sharon Kennedy
(74) *Attorney, Agent, or Firm*—Blakely, Sokoloff, Taylor & Zafman LLP

(57) ABSTRACT

An increase in agent residence time at a tissue site is provided for by the presence of a barrier. The barrier is a separate entity from the agent when introduced to the tissue. A binding member is included in the barrier for coupling the barrier to the surface of the tissue. In one embodiment, agent is introduced to the tissue prior to attachment of the barrier to the tissue. In another embodiment, agent is presented after the barrier is positioned on the tissue surface. A delivery vehicle may be used to administer the agent and barrier to a patient.

18 Claims, 6 Drawing Sheets

OTHER PUBLICATIONS

H. Ohigashi M.D., et al., "A New Method of Intra–Arterial Regional Chemotherapy With More Selective Drug Delivery For Locally Advanced Pancreatic Cancer," Hepatogastroenterology, Mar.–Apr. 1996, pp. 338–345, vol. 43:8.

E.H. Tan, et al., "5–Fluorouracil Continues Infusion In Metastatic Colorectal Cancer," Ann. Acad. Med. Singapore, Sep. 1996, pp. 748–751, vol. 25:5.

D. Stephan, et al., "A New Cationic Liposome DNA Complex Enhances the Efficiency of Arterial Gene Transfer In Vivo," Hum. Gene Ther., Oct. 1, 1996, pp. 1803–1812, vol. 7:15, Mary Ann Liebert.

D. Brieger et al., "Local Drug Delivery Systems and Prevention of Restenosis," Cardiovasc. Res., 1997, pp. 405–413, vol. 35, Elsevier Science B.V.

S. Bailey, "Local Drug Delivery: Current Applications," Progress in Cardiovascular Diseases, Sep./Oct. 1997, pp. 183–204, vol. 40:2.

V. Bhat, et al., "Improving Endothelial Cell Adhesion to Vascular Graft Surfaces: Clinical Need and Strategies," J. Biomat. Sci. Polymer. Edn., 1998, pp. 1117–1135, vol. 9:11.

Sturgeon, C. M. "The Synthesis of Polysaccharide Derivatives," Carbohydrate Chemistry, 1988, Chapter 13, Oxford University Press, New York.

V. Bhat, et al., "Using Avidin–Mediated Binding To Enhance Initial Endothelial Cell Attachment and Spreading," J. Biomed. Mater. Res., Apr. 1998, pp. 57–65, vol. 40:1, John Wiley & Sons.

V. Bhat, et al., "Fibronectin and Avidin–Biotin as a Heterogeneous Ligand System For Enhanced Endothelial Cell Adhesion," J. of Biomed. Mater. Res., Sep. 5, 1998, pp. 337–385, vol. 41:3, John Wiley & Sons.

* cited by examiner

PROCESS FOR AGENT RETENTION IN BIOLOGICAL TISSUES

FIELD OF THE INVENTION

The present invention relates generally to the enhancing retention of substances in biological target site, and more particularly to applying a chemical barrier for prolonging agent residence time in a biological tissue.

BACKGROUND

The medical and veterinary fields have long used agents to treat, diagnose and prevent countless medical conditions. The substances are used to alter the body's function at the molecular level. The types of agents that are administered to biological systems include natural and synthetic drugs, biological agents, therapeutic radiation, and the like.

There are many complications that accompany the use of agents. The efficacy of chemical treatment depends on several variables including (1) the mechanism of chemical reaction, (2) penetration of the chemical into a target site, (3) amount of chemical that is delivered, (4) proficiency of delivery, and (5) residence time of the chemical at the target site.

The composition of the chemical is one factor that impacts these variables. Enormous efforts are placed on devising new and improved compounds. In particular, chemicals are formulated for providing optimal reaction mechanisms and penetration.

The agent's route of administration and travel to the treatment site further influence the variables to efficacy. Traditional routes of administration include intravenous, oral, inhalational, topical, transdermal, subcutaneous, intramuscular, buccal, intra-arterial, intrathecal and rectal.

Methods of directly administering an agent are of special interest. Such local applications reduce the distance through which the agent must travel between the site of administration and the intended target place. As a result the chemical has a higher bioavailability at the target site. Unlike systemic delivery, local delivery of chemical can be made at high concentrations without causing systemic toxicity issues. Where the agent must extensively travel through the body to reach the target tissue, the agent may be metabolized in the gut, portal blood or liver prior to entry into other systemic circulation. Moreover, an agent flowing through the circulation to reach its proposed destination may be retained by blood plasma proteins instead of binding to its intended tissue protein. Direct routes are also useful for reducing potential undesirable effects, producing high local concentrations of agent at the treatment site, and continuously attending to chronic conditions.

In order to enhance chemical performance, medical devices are constructed and medical procedures devised to facilitate contacting the agent with its target site. For example, many devices and methods have been designed to increase agent penetration, the amount of agent delivered and the efficiency of chemical function.

Special routes of administration are available for dispensing agents directly to a target tissue. The agents may be attached to a carrier that is implanted near the target site, e.g. drug delivery stents. Other local agent delivery devices include microporous balloon catheters, ultrasound-enhanced delivery through microporous balloons, intra-vascular injection catheters, iontophoresis, etc. Intra-vascular, intraoperative or intrathecal catheters may also be surgically inserted near the target organ for delivery of agents. In an exemplary case, gene therapy agents are presented to the heart through a catheter that is percutaneously introduced, such as through the femoral artery, and guided upstream into the left ventricle and epicardium for agent introduction into the pericardial space. In such procedures, access to the pericardium may also be gained intra-vascular or through a thoracotomy.

Once an agent is administered, the chemicals progress throughout the body to and from the target site via the bloodstream, diffusion and active transport systems. Most fluids move freely through the circulatory system and pass to various areas of the body through capillaries. There are some natural barriers that restrict movement of molecules throughout the body, such as the blood-brain barrier for hindering the passage of selective chemicals to the brain. Most capillaries, however, have vessel walls with cells arranged in a manner that allow molecules as large as 20,000–30,000 Daltons to pass under pressure through the vessel wall.

After an agent reaches its intended treatment site, it is typically absorbed by blood vessels and washed away with circulating blood flow. Agents are then usually excreted from the body by transfer via the circulation to the kidneys, liver, gastrointestinal tract, lungs, salivary glands and sweat glands.

However, frequently an agent is only effective while it is in contact with the target site, e.g. bound to a receptor. Mechanisms that resist removal of an agent by circulating blood flow permit the agent to create a more dramatic outcome at the treatment site. Prolonged agent retention times at the target location enhance many treatments, especially those requiring long-term administration of agent. Moreover, since less agent is quickly washed away with these methods of increasing agent retention, a smaller amount of agent is required. Hence, the cost of the agent is reduced. Furthermore, the lower dosage of agent may decrease side effects that sometimes occur with larger amounts.

Many medical conditions benefit from prolonged agent residence time at the target site, such as cardiac conditions. Coronary heart disease is the most common disease and cause of death in civilized, western countries. In the treatment of atheroslerotic coronary disease, percutaneous transluminal coronary angioplasty (PTCA) may be performed to reduce obstructions in a vessel. PTCA involves the introduction of a catheter with a small dilating balloon at its tip. The catheter is snaked through the arteries, often in the arm or leg, to a site where the vessel has narrowed. The balloon is inflated to increase the cross-sectional area of the vessel.

Although PTCA treatment has a high success rate in widening the vessel, often the vessel re-narrows or re-closes post dilation, referred to as "restenosis." In restenosis, proliferation of smooth muscle cells does not initiate until a long time (48–72 hours) after the PTCA procedure is performed. Treatment of restenosis includes delivery of anti-proliferation drugs to the site of the diseased vessel wall following PTCA and during the same surgery. Yet, the drug treatment is only mildly effective because the bloodstream removes the drug from the tissue quicker than the time it takes for the onset of restenosis. The drug is encouraged to diffuse out of the area of higher agent concentration in the vessel walls to the site of lower concentration in the internal lumen of the vessel. The flowing blood maintains this lower agent concentration inside of the vessel. In this manner, the agent is readily washed away from the target site and agent has a limited residence time in the tissue.

Current approaches to increase chemical retention times involve manipulating the agent prior to its introduction into a biological system. Typically, functional molecules are pre-attached to the agent to alter the physical structure of the agent in a manner that hinders absorption of the agent after it is delivered into the blood stream. In one such technique, a polyanionic sulfate group is bound to a drug in order to impart negative charges. The negatively charged drug repels from the negatively charged walls of a capillary and resists absorption onto the vessel wall. Thus, the agent is retained within the peripheral circulation.

Some retention systems attempt to provide for gradual release of an agent from a delivery source. Prior to administering, an agent may be coupled to a carrier that slows the release of the agent at the target site. One exemplary system binds a drug to an ionic carrier for administering to the eye. Tear fluid gradually dissolves the carrier to release the drug. Other systems include microcapsules that encapsulate the drug. The shell is biodegradable, such as by hydrolysis, to slowly release the drug.

In other methods, a drug is pre-incorporated into a solid polymeric material that is inserted into a vessel. Once the material reaches the target site, the material is reconfigured to form a support structure on the vessel surface. For example, the solid material may be heated to melt the material, molded to the shape of the internal vessel surface and then re-solidified. A problem with this system is that the manipulation of the material once it is in the vessel, such as by heating, may disrupt the agent and vessel.

There are many problems with these current systems that require the agent be structurally manipulated prior to entry into the body. A significant drawback to the use of pre-altered agents is that modification of each chemical agent is complicated and expensive. Retention mechanisms and attachment structures must be tailored for each agent of interest. The resulting change in molecular structure of the agent composition may compromise chemical action. Furthermore, pre-attachment of a delivery component to the agent results in an increased size of the agent composition. This altering of the agent may hinder penetration or delivery of the chemical.

Moreover, carrier systems do not lengthen the time that agent molecules contact a target site, but rather provide a constant supply of agent to a site. Thus, these systems require large amounts of agent in order to lengthen the effect. These carrier systems are also limited by the amount of agent that may be administered in the vehicle.

In view of these limitations with current systems, there is a need for a platform for prolonging chemical residence time that may be applied universally across a variety of agents. Furthermore, a system is desired which lengthens agent effect by extending the time in which agent molecules contact a site, rather than increases the agent dosage. The mechanism should not hinder chemical reaction, penetration or delivery and cause minimal damage to the tissue. In particular, an approach for hindering reabsorption of an agent by the bloodstream without manipulating the agent prior to administering would be advantageous.

SUMMARY OF THE INVENTION

An agent retention system and process is provided for prolonging the residence time of an agent in, on or near a tissue. In general, the system increases agent effectiveness at a treatment site by extending the time in which agent molecules contact the site, rather than increasing the agent dosage. The tissue that benefits from the retention system may be any biological tissue having at least one surface. For example, the tissue may be a vessel, organ, tumor cells, or the like.

A biodegradable barrier that is separate from the agent is utilized in the present invention the barrier has a binding member to couple the barrier to a tissue surface. The barrier may be a biodegradable molecule that is biocompatible with the target tissue. For example, the barrier may be a poly (anino acid), such as poly-L-lysine. The binding member permits attachment of the barrier to the tissue surface by a variety of binding mechanisms, such as ionic binding, covalent binding, electrostatic interactions, hydrogen bonding, and the like. For example, the barrier's binding member may be a cationic ion for binding to an anionic member of the tissue surface. In one embodiment of the barrier, a charged binding member is included for adhering to an oppositely charged member on an interior vessel surface and a passive platelet inhibitor.

In one embodiment of the agent retention method according to the present invention, a pre-treatment agent is contacted with the tissue, followed by contact with the barrier to the tissue surface. A sufficient amount of the barrier is allowed to adhere to the tissue surface to hinder diffusion of the agent through the tissue surface as compared to diffusion of the agent without the presence of the barrier.

In some cases, the barrier is contacted with a tissue surface prior to introduction of a post-treatment agent. In this embodiment, the post-treatment agent is contacted with the barrier and the agent attaches to the barrier. The agent is retained at the tissue for a prolonged period of time as compared to the retention of the agent without the presence of the barrier.

In still other configurations, the retention system is applied to a tissue having an inner tissue wall and tissue surface. The agent and biodegradable barrier are administered to a patient in a time-varied manner. A sufficient amount of the barrier's binding member is allowed to couple the barrier to the tissue surface to hinder diffusion of the agent through the tissue surface.

The barrier composition may be formulated by admixing a barrier having a binding member and a delivery carrier. The barrier component is present in an amount sufficient to couple to the tissue surface and to permit transport of the agent from the tissue surface at a lower rate than agent transport in the absence of the barrier composition.

The retention system may comprise the barrier and a conduit, e.g. a catheter, having at least one opening for administering the agent and barrier. The barrier, agent and optionally the conduit may also be included in a system for increasing agent residence time in a tissue.

The benefits of the agent retention system are direct in that the system may be universally applied across a variety of agents. With the present retention system, any pre-treatment agents may be retained for longer in the tissue. Agent need not be reformulated with the barrier or even compatible with the barrier. In one embodiment, the approach hinders reabsorption of an agent by the bloodstream without needing to manipulate the agent prior to administration into a patient.

The mechanism for agent retention according to the present invention does not hinder chemical reaction, penetration or delivery of the agent. The process further may result in only minimal damage to the tissue.

Other features and advantages of these and other embodiments are discussed in detail below.

BRIEF DESCRIPTION OF THE DRAWINGS

The present invention is illustrated by way of example, and not limitation, in the figures of the accompanying drawings in which:

FIG. 1 illustrates a cross-sectional view of a vessel having a pre-treatment agent and one embodiment of a barrier configured in accordance with the teachings presented herein.

FIG. 2A shows a barrier on one surface and a post treatment agent and FIG. 2B shows a barrier attached to two tissue surfaces and the tissue includes a pre-treatment agent and post-treatment agent, in accordance with the teachings presented herein.

FIG. 5A shows data from a proximal section and FIG. 5B shows data from a mid section.

DETAILED DESCRIPTION

Figure 1:
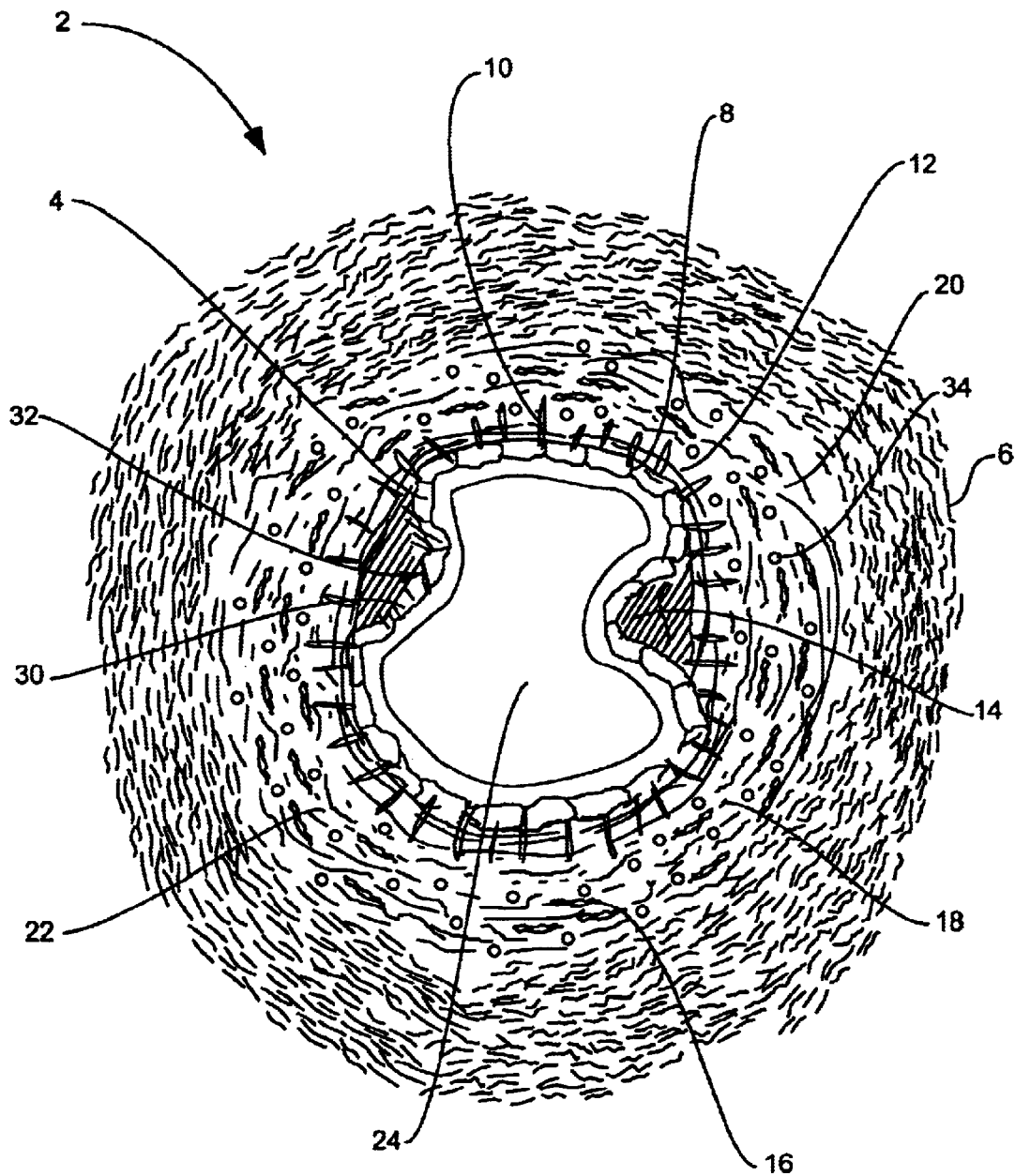

A method for enhancing the residence time of an agent in biological tissues using a barrier composition is provided. It has been discovered that the attachment of a barrier to a tissue surface hinders diffusion of an agent into circulating fluids thereby increasing the retention time of the agent in the tissue compared to the retention time of the agent in the absence of the barrier. The barrier of the present invention is applied to the tissue surface with a delivery vehicle. The barrier has a binding member for attaching to the surface. According to the method of using the retention system as per to the present invention, agent may be administered to the tissue prior to the introduction of the barrier to the tissue. In another embodiment, post-treatment with an agent allows agent to attach to the barrier residing on the tissue surface.

The barrier may be used with any human or animal tissue that may benefit from prolonged residence of an agent at a tissue site, i.e. within the tissue matrix, on the tissue surface or in proximal location to the tissue. Often, the tissue has a cavity and the barrier is coated on the cavity contacting surface to hinder passage of an agent from or into the cavity. Arteries, veins, ureters, urethras, bronchi, biliary and pancreatic duct systems, gut, nasolacrimal ducts, sinus cavities, eye and eustachian, spermatic and fallopian tubes are within the contemplated sites for treatment using the methods and materials of the present invention. However, other tissues that have accessible surface area for barrier attachment may also be used with the retention barrier and process.

The tissue may also be representative of the condition being treated, such as a tumor, where the agent is injected into the tumor and the barrier attaches to the tumor surface. The present invention may increase the residence time of anti-cancer drugs locally delivered to the site of cancer. In one example, Methotrexate and Angiotensin II are delivered to cells in exocrine pancreas during a laparotomy. The drugs are administered through catheters in the splenic artery and gastroduodenal artery to halt cell proliferation and decrease blood flow to the cancer cells. For more information on treatment of pancreas cancer, see "A New Method Of Intra-Arterial Regional Chemotherapy With More Selective Drug Delivery For Locally Advanced Pancratic Cancer," Hepatogastroenterology, 43:8, 338–345, March–April 1996.

The term "tissue surface" or any variation thereof, refers to the outer lining of the walls of a tissue. Tissue surfaces include the area of cells that occupy the outside of tissue walls, e.g. endothelial cells and matter attached to the outer cellular layer, i.e. extracellular matter, such as collagen, proteoglycans, glycoproteins, elastin, fibrin, plaque, agent, other molecules, or combinations thereof. In some embodiments of the retention process, binding groups are bound to the external cellular layer prior to contact with the barrier to form the tissue surface.

One exemplary tissue is a human vessel, as shown in FIG. 1. The wall of the vessel 2 has an endoluminal tissue surface 4 and outer tissue surface 6. The endoluminal tissue surface 4 includes both endothelium cells 8 and patches of plaque 14 that enclose a luminal space 24. Such luminal space 24 provides for the flow of circulating fluids, e.g. blood and lymph, and other molecules traveling in the fluids. The endothelium cells 8 and an elastic tissue layer, called the lamina elastica interna 10, include the tunica intima 12. The tunica media 20 surround the tunica intima 12 and is composed of varying proportions of smooth muscle 16 and elastic tissue 18. The outer investment is the fibrous tunica adventitia 22 to form the outer tissue surface 6.

The attachment of the barrier is independent of the internal structure of the tissue walls, so the barrier may be effective for use with any variation of vessel. The general structure of the vessel depicted in FIG. 1 may be representative of any artery or vein, since either vessel has similar layers in its wall. Some variations among vessels include more elastic tissue in the tunica media of large arteries and more smooth muscles in this inner layer in small arteries. Also, the tunica media of veins is typically lean in smooth muscle and elastic tissue. Many large veins have a thick tunica adventitia including elastic tissue and smooth muscle along with collagenous fibers.

Barrier

FIG. 1 depicts one embodiment of a barrier 30 bound to endoluminal tissue surface 4. The barrier includes a binding member 32 that adheres to the tissue surface. However, in other embodiments, a portion of the barrier may also partially enter the tissue walls close to tissue surface. For example, some barrier may be absorbed into the tunica intima 12. In the vessel of FIG. 1, a pre-treatment agent 34 is embedded in tunica media 20. The barrier 30 hinders the pre-treatment agent from diffusing through the endoluminal tissue surface 4 and into the luminal space 24 where agent is washed away by circulating fluids. Typically in most vessels, the fibrous texture of the tunica adventitia 22 discourages the agent from diffusing through the outer tissue surface 6. Thus, the pre-treatment agent remains in the tissue walls longer than the agent would without the barrier present.

The barrier must be biocompatible with the tissue. The barrier is chosen to cause minimal adverse side effects to the body. Natural barrier compositions are advantageous. Prior to the barrier's introduction into the body, the barrier is a separate entity from the agent. Thus, the agent and barrier are not reformulated to include the other in the material's structural composition. Nor is the barrier bound to the agent before the barrier is administered. Although the barrier and agent may be administered in the same delivery vehicle, usually they are sequentially introduced at the target site.

Typically, the barrier is biodegradable and therefore non-permanently bound to the tissue surface. The material may be removed from the biological system by natural or imposed therapeutic, biological and/or chemical processes. The choice and amounts of barrier may be varied for particular stability times. The duration of barrier attachment depends on the particular application of the retention process. For example, a suitable barrier for use in treatment of restenosis would be stable for a few (about 24 to 48 hours) days after PTCA. Immediately after the PTCA catheter procedure, the body produces toxic cytokines in an attempt to heal itself. It is understood that the released cytokines play a major role in the onset of restenosis about 6 months later. See Prospects for Site Specific Delivery of Pharmacological and Molecular Therapies, by Riessen and Isner, J. Am. Col. Card. Vol 23:5 April 1994, pgs. 1234–1244; Local Drug Delivery Systems and Prevention of Restenosis, by Brieger and Topol, Cardiovasc. Res. Vol. 35, 1997, pgs. 405–413. With the use of the agent retention process, a proliferative drug and barrier may be administered during the PTCA operation and the drug may be maintained by the barrier at the treatment site for a period of time thereafter, e.g. during the course of recovery.

Usually, the barrier is fluent as it is applied to the tissue. It is desirable that the phase state of the barrier does not become altered with the attachment of the barrier molecules to the tissue.

Further to the particulars of the barrier, a binding member is included in the barrier for attachment to the tissue surface. There are many types of binding members and attachment mechanisms suitable for coupling the barrier to the tissue surface. With polar compositions, the binding member is an ionic charged member of a pair that is opposite from the charge of an ionic member provided on the tissue surface, where attachment is by ionic bonding. The binding member may be a cationic member and the tissue surface includes an anionic member. For example, typical endothelial cells are negatively charged and serve as an anionic member on the tissue surface. A cationic binding member of the barrier attaches the barrier to the cells on the surface. Similarly, the tissue surface may be cationic and an anionic binding member in the barrier serves to anchor the barrier.

In another embodiment, charged molecules are pre-attached to the tissue surface prior to binding of the barrier. For instance, a negatively charged member, such as carboxylic acid, sulfonic acid, halogenated alcohols, phenolic hydroxy and acidic hydroxy groups, and the like, may be contacted with and bound to the surface endothelial cells or other surface molecules. In other cases, positively charged members, such as amino and imino groups, and the like, are bound to the surface and the barrier includes an anionic member.

Where the attachment mechanism is ionic binding, there are advantages to using barriers which are ionically charged at or near neutral pH's, such as pH of about 6–10 and more usually pH of about 7. Thus, barriers with cationic or anionic binding members having pKa values between 6 and 10 may be of preference. Such barriers would be slower to degrade after attached in vivo, for example, by neutralization of the barrier in the body's natural pH. In vivo pH levels at the tissue may also be controlled for barriers with charged members having $pK_a$ values outside of the physiological range. Furthermore, during in vitro assays, the environmental pH level may be optimized to be strongly acidic or basic, depending on the binding member's $pK_a$ to accommodate the anionic or cationic forms.

In still other embodiments of barriers, a binding member on the barrier shares electrons with a member of the tissue surface to form a covalent bond. In this manner, barrier is incorporated into the tissue surface and to produce a new molecule. In one example of covalent binding of barrier, N-hydroxysuccinimide biotin molecules are covalently attached to lysine groups in the cell membrane. For more information on covalent binding, see "Using Avidin-Mediated Binding To Enhance Initial Endothelial Cell Attachment And Spreading," J. Biomed. Mater. Res., 40:1, 57–65, April 1998.

Binding may further be due to electrostatic interactions, hydrogen bonding or other receptor to ligand non-covalent binding. For example, agarose gels may be used in various sustained released drug delivery may be stabilized by hydrogen bonding. See "The Synthesis of Polysaccharide Derivatives," in Carbohydrate Chemistry, Oxford University Press, 1998. In another example, avidin and biotin increase adhesion of endothelial cells on vascular grafts via a strong non-covalent bond ($K_D=10^{-15}$ M). See "Improving Endothelial Cell Adhesion To Vascular Graft Surfaces: Clinical Need And Strategies," J Biomat. Sci. Polym. Ed. 9:11, 1117–1135, 1998 and "Fibronectin and Avidin-Biotin As A Heterogeneous Ligand System For Enhanced Endothelial Cell Adhesion," J. Biomed. Mater. Res., 41:3, 337–385, Sep. 5, 1998.

In some applications, the barrier further includes enhancing components to facilitate the treatment process. In one embodiment, the enhancing component may be combined with the barrier prior to introduction of the barrier into the body. In another embodiment, the barrier is administered to the body, and then the enhancing component is added. In sequential administrations, the enhancing component adheres to the barrier after the barrier attaches to the tissue surface. One exemplary enhancing component, a passive platelet inhibitor, may be combined with the barrier to discourage platelets from forming on the tissue wall, e.g. vessel wall. Passive inhibitors, such as albumin, PEG and IgG, block attachment of platelets. Negatively charged albumin is especially useful with cationic barrier compositions. By contrast, active inhibitors, such as heparin, work after platelets have attached to a surface and render the present platelets non-functional. The combination of barrier and platelet inhibitor as applied to a vessel wall, provides the dual advantage of hindering the agent from being washed away with flowing blood and discouraging clotting of blood in the vessel at the treatment site.

There are many varieties of barriers, both naturally occurring and synthetic, suitable for use in the retention process. Some exemplary barriers are shown in Table 1. Where the barrier is a water-soluble amino acid, the binding member is usually a charged group and more usually a cationic member that is near physiological pH's. In one embodiment, the barrier is a monocationic form of lysine with binding member, aminium group $NH_3^+$ and having a $pK_a$ of 9.0. The barrier may also be a lysine in a dicationic form with the carboxyl group having a $pK_a$ of 2.2. Other polar amino acid barriers having acidic or basic binding members are glutamic acid, arginine and aspartic acid.

Usually, the barrier is a polymer chain of amino acid residues, such as dipeptides, tripeptides, oligopeptides and polypeptides. Poly(anino acids) are of special interest because they show a low level of systemic toxicity after their degradation to naturally occurring amino acids, creating minimal harm to the body. The term "naturally occurring," is a term of the art referring to compositions that are produced by a biological system. The amino acid barriers are usually the naturally occurring L-amino acid racemic form. For example, poly-L-lysine and poly-L-glutamic acid may be used. A barrier with passive platelet inhibitor is poly-L-lysine acid with albumin. (Poly)amino acids have been described for use as suture materials, artificial skin substitutes and drug delivery systems. See "Biomaterials Science, Introduction to Materials and Medicine," by Ratner, Academic Press, 1996, pgs. 68–69. The use of such (poly)amino acids as barriers to agent transport, avoids many of problems that may occur when using the compositions in polymer based devices Furthermore, polycations have been used to coat devices for drug delivery carriers. In particular, poly-L-lysine has been shown to increase nitric oxide production leading to vasodilation. In some applications, this promotion of nitric oxide by poly-L-lysine barriers is of special interest for use in blood vessels, where blood flow may be increased through an otherwise occluded vessel.

TABLE 1

| Barrier | $pK_a$ $CO_2H$ | $pK_a$ $NH_3$ | $pK_a$ R Group |
|---|---|---|---|
| Lysine | 2.2 | 9.0 | 10.5 |
| Arginine | 2.2 | 9.0 | 12.5 |
| Histidine | 1.8 | 9.2 | 6.0 |
| Glutamic Acid | 2.2 | 9.7 | 4.3 |
| Aspartic Acid | 2.1 | 9.8 | 3.9 |
| Glycine | 2.3 | 9.6 | |
| Alanine | 2.3 | 9.7 | |
| Valine | 2.3 | 9.6 | |
| Leucine | 2.4 | 9.6 | |
| Isoleucine | 2.4 | 9.7 | |
| Phenylalanine | 1.8 | 9.1 | |
| Asparagine | 2.0 | 8.8 | |
| Glutamine | 2.2 | 9.1 | |
| Tryptophan | 2.4 | 9.4 | |
| Proline | 2.0 | 10.6 | |
| Serine | 2.2 | 9.2 | |
| Threonine | 2.6 | 10.4 | |
| Tyrosine | 2.2 | 9.1 | 10.1 |
| Hydroxyproline | 1.9 | 9.7 | |
| Cysteine | 1.7 | 10.8 | 8.3 |
| Cystine | 1.6 | 7.9 | |
| Methionine | 2.3 | 9.9 | |

Other useful barriers include backbone-modified "pseudo"-poly(amino acids), such as polyester from N-protected trans-4-hydroxy-L-proline, poly (iminocarbonate) derived from tyrosine dipeptides, and tyrosine-derived polycarbonates. Further exemplary ionic barriers with basic side group binding members (amino and imino groups) are poly(vinyl amines) such as polyethyleneimine, poly(vinylamine) and poly(allyl amine); poly(vinyl pyridine); poly(vinyl imidazole), etc. Suitable anionic barriers include chemicals with acidic side groups for binding members, such as carboxylic acid, sulfonic acid, halogenated alcohols, phenolic hydroxy and acidic hydroxy groups. Exemplary anionic barriers are poly(phosphazenes), poly(acylic acids), poly(methacrylic acids), copolymers of acrylic acid and methacrylic acid, poly(vinyl acetate), sulfonated polymers such as polystyrene, combinations thereof, and the like The present method anticipates the use of still other barriers including polymers and proteins. All of the aforementioned barriers are by way for example, and are not intended to limit the choices that are or may become available in the art.

Agent

In general "pre-treatment" agent refers to agent contacted with the target site, e.g. tissue, before the barrier contacts the tissue. Similarly, "post-treatment" agent refers to agent that is contacted with the target site, e.g. tissue, after the barrier contacts the tissue. The retention system may be used to prolong the residence time of any convenient agent that assists in diagnosis, research, therapy and disease prevention. The agent may be naturally and synthetically occurring substances, drugs, growth factors, gene therapy compositions, chemotherapeutic chemicals, anti-bacterial chemicals, ions, cells, small and large molecules, other agents, and any combination thereof. The term, "drug" is a chemical capable of administration to an organism which alters the organism's physiology. Drugs include well recognized pharmaceutical, such as those listed in "Drug Facts and Comparisons", $4^{th}$ ed. 2000; "The Physicians Desk Reference," $49^{th}$ ed., 1999; "Goodman and Gilman's The Pharmacological Basis of Therapeutics" $9^{th}$ ed. (1995), pgs. 103–1673; and "The United States Pharmacopeia, The National Formulary," USP 23 NF 18 (1995) Drugs also include compounds that have indicated properties that are not yet formally recognized. Usually the agent is therapeutic in nature. The agents may be useful in pre-treatment and/or post-treatment of tissue with the barrier, where the pre- and post-treatment agent may be the same or different chemicals and concentrations.

In particular uses, the agent may be an anti-proliferative drug for inhibiting cell proliferation, e.g. antibiotics, anti-metabolites, cytotoxic agents, steroids, hormones, anti-parasitic, anti-platelet, anticoagulants, calcium channel blockers, anti-hyperlipermics, receptor blockers, anti-connective tissue agents, anti-smooth muscle agents, and endothelial growth stimulators. More specifically the anti-proliferative agent may be Taxol® from Bristol-Myers Squibb Co. located in N.Y.; Taxotere® from Rhone-Poulenc Rorer S.A. located in Antony, France; Heparin Sodium from Pharmacia & Upjohn Co. located in Michigan and Cosmogen from Merck & Co. located in N.J. Furthermore, the agent may be anti-thrombotic, anti inflammatory, anti-fibrotic, anti-migratory and immune suppressive agents.

In other specific applications the agent is a vector containing DNA capable of expressing a therapeutically or diagnostically useful protein, such as the gene therapy agent described in U.S. Pat. No. 5,797,870.

The aforementioned agents are by way of example and are not intended to limit the choices of agents that are or may become available in the art for contact with the target tissue.

Delivery Vehicle

The retention system according to the present invention includes a delivered vehicle for administering the barrier. The same or different vehicles may be used to dispense the agent and barrier. At times, the barrier is directly administered to the target site with a conduit and a post-treatment agent is administered by widespread perfusion of the area. For example, the body may receive a systemic, intravenous injection of the post-treatment agent. At other times, both the pre-treatment agent and barrier are directly applied, for example, with a conduit.

In general, a myriad of conventional mechanism for conveying the barrier and/or agent to the tissue surface may be used. These delivery devices may transport the barrier or agent by pressure, mechanical force, gravity, diffusion, etc. In some applications it is advantageous for the delivery device to swiftly apply the barrier to the target tissue before the agent escapes through the tissue. Thus, injection mechanisms and quick diffusion devices may be preferred. However, the scope of the invention also intends devices for gradual administering of the barrier, e.g. sustained release devices. Typically, the delivery device allows the materials to be directly applied to the target tissue, such as the walls of a coronary artery, although devices for indirect procedures may be employed as well.

Some exemplary techniques for applying the materials include invasive surgical procedures and minimally invasive surgical procedures, such as laparoscopic processes and percutaneous transluminal processes. Preferably the deliver device for administering the barrier is the same device that is used to present the agent.

In one embodiment, the barrier and agent are applied by use of a conduit, such as a catheter. The catheter may include any number of balloons and lumens. A single lumen may be present and accommodate a guide wire, the stream of fluid being delivered, and optionally pressure, for example where a balloon is present with microporous holes for fluid release. In other embodiments, the guide wire and fluid are carried in one lumen and a second lumen is used to apply pressure. Where no pressure is applied to the conduit, one lumen may contain the guide wire and a second lumen for a fluid stream. The conduit is sized and shaped to fit inside of the appropriate area of a body.

The conduits that may be useful in the present invention may be variations of the catheters described below that are known or will be developed in the art, e.g. standard angioplasty catheters, infusion catheters and local drug delivery catheters. Some suitable conduits include Rapid Exchange (Rx) Dilation Catheters, Perfusion Catheters, and Over-The-Wire Catheters, all from Guidant Corporation, located in Santa Clara, Calif.

In alternative embodiments of agent retention system, different types of delivery conduits may be used and embodied in a variety of ways. Various conduits use mechanical forces to inject materials. For example, iontophoretic balloon catheter (by Cortrak Medical, Inc., located in St. Paul, Minn.) and needle catheter by (BMT Ltd.) may be employed. Some delivery devices use passive diffusion to administer material. Passive conduits include double balloon catheters, coil balloon catheters, hydrogen balloon, and stent coatings. Furthermore, a combination of driving forces, such as microneedles on balloons using pressure with punctures and microporous balloons with a phono-device using pressure, diffusion and ultrasound.

The present invention anticipates still other conduits. All of the aforementioned conduits are by way of example, and are not intended to limit the choices that are or may become available in the art.

In still other embodiments the delivery vehicle is a time-release matrix, time-release coating, companion ions, etc. The barrier and agent may be presented in the same pharmaceutical carrier where timed release of the barrier and agent is controlled. Successive administration may be carried out in carriers having different coatings with contrasting time constants for release of the barrier compared to agent release.

Other Embodiments of the Retention System

Figure 2A:
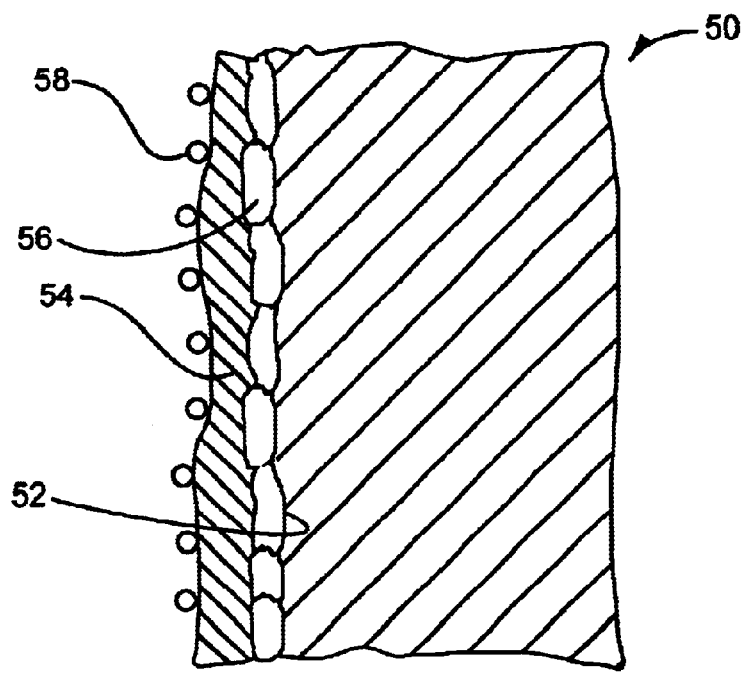
FIGS. 2A–2B illustrate a cross-sectional views of a tissue with other embodiments of barriers, where
Figure 2B:
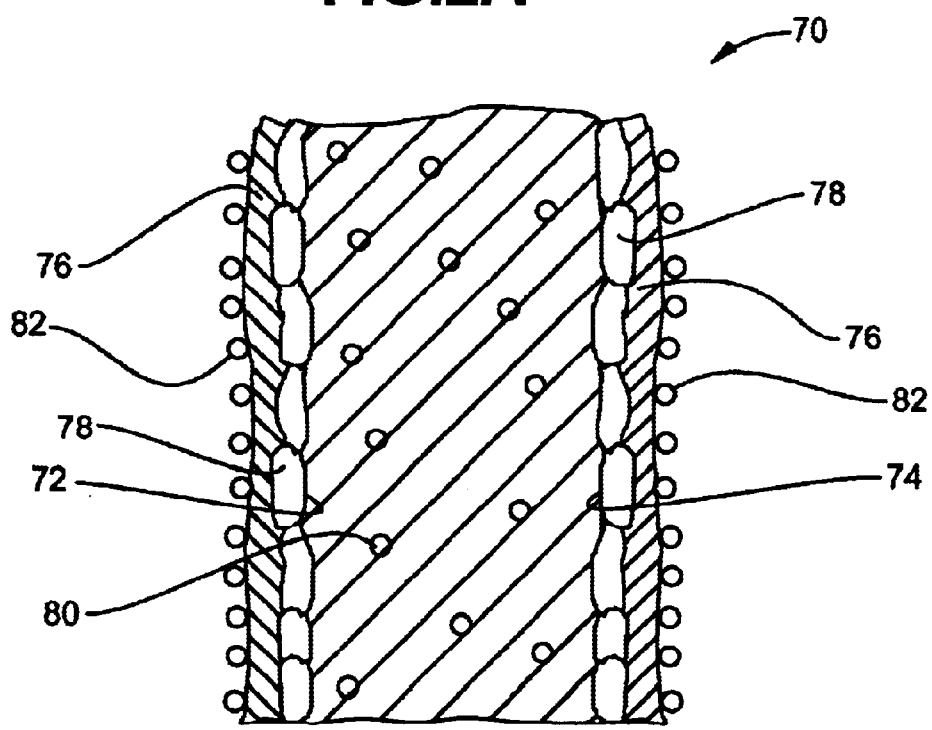
Figure 3:
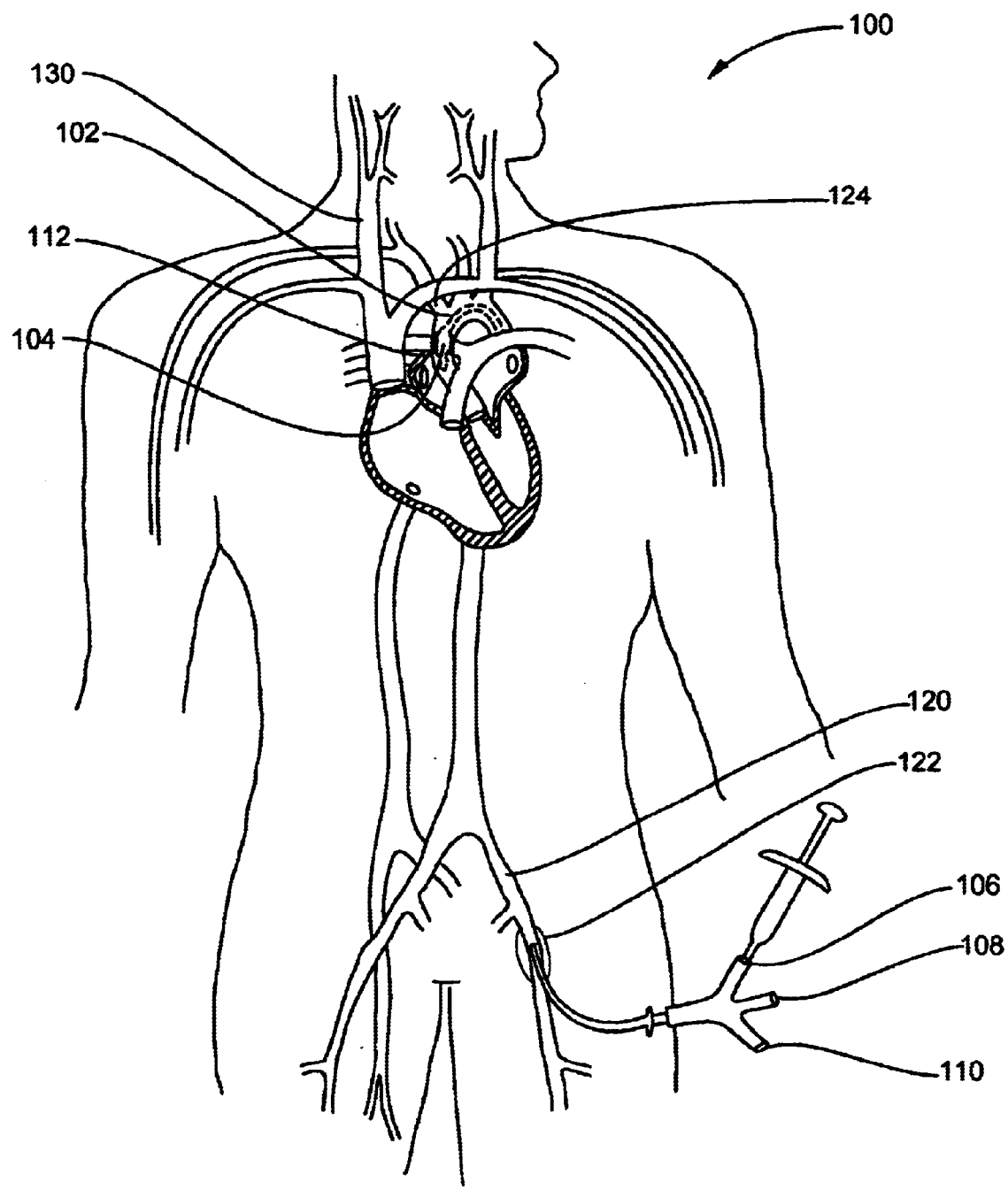
FIG. 3 illustrates the implementation of a device for delivering an agent and barrier to a coronary vessel.
Figure 4A:
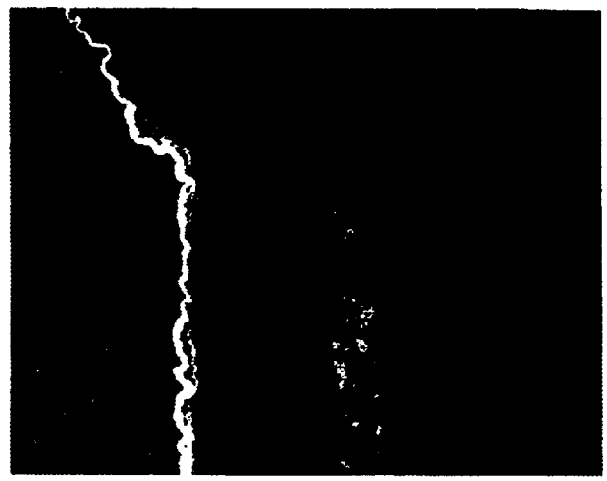
FIGS. 4A and 4B are images of tissue sections exposed to a pre-treatment agent.
Figure 4B:
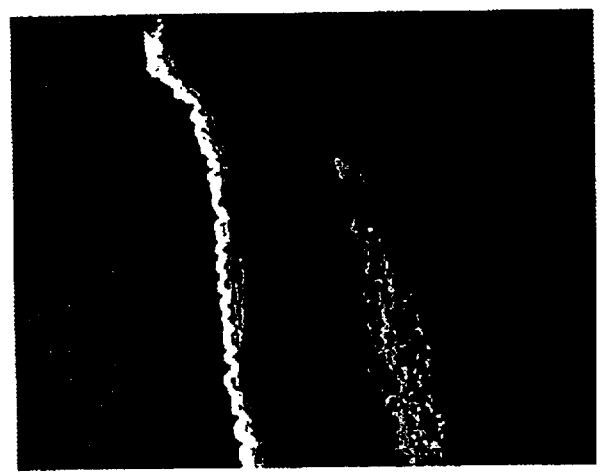
Figure 5A:
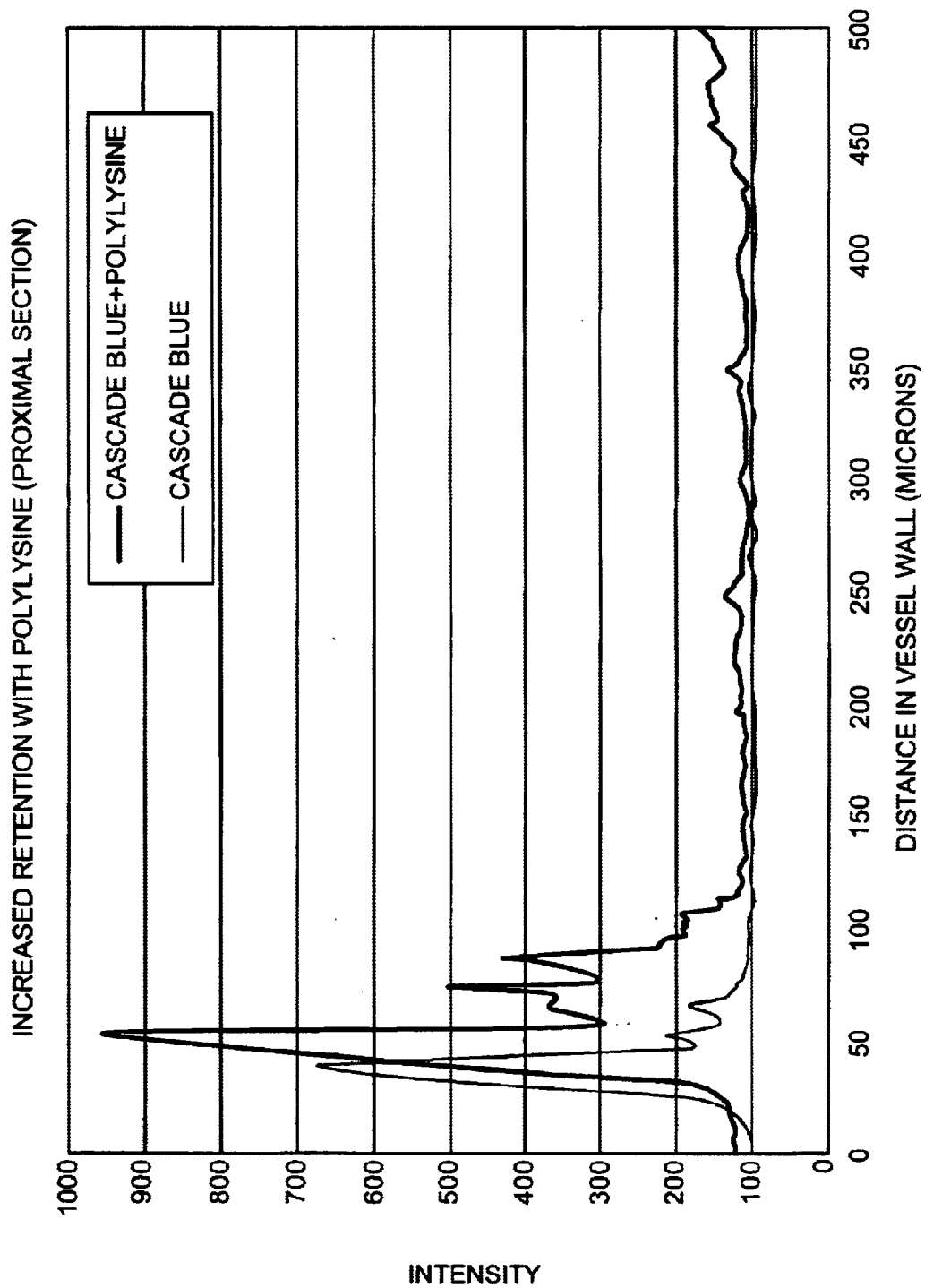
FIGS. 5A and 5B are graphs of increased agent retention in sections of tissue with the presence of barrier compared to agent in the tissue without barrier, where
Figure 5B:
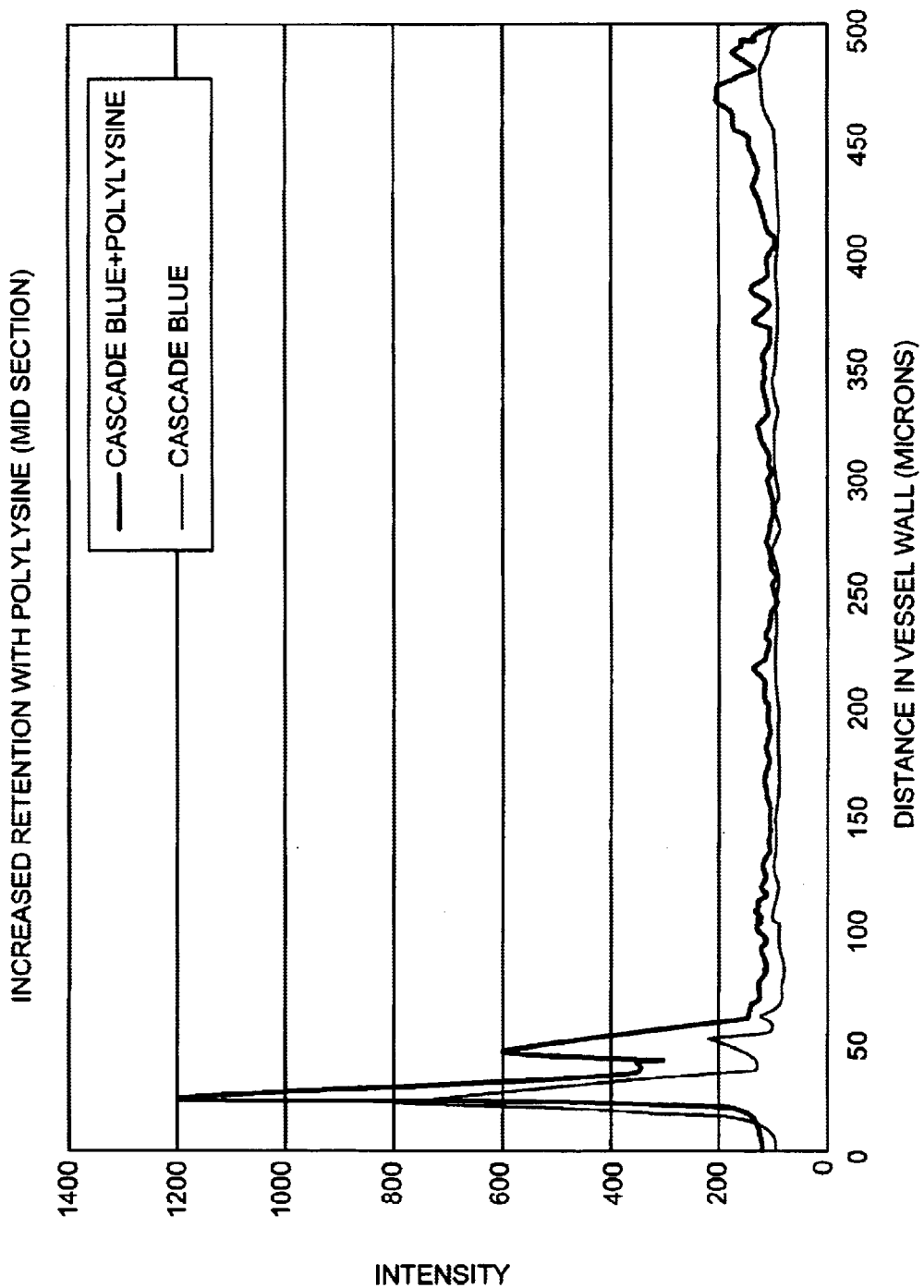

Alternative embodiments of the retention process may be used to apply agent and barrier in various configurations, as shown variously in FIGS. 2A and 2B. FIG. 2A shows a cross-sectional view of a tissue coated by one embodiment the retention process. The tissue 50 has a barrier 54 attached to tissue surface 52 by binding member 56 and a post-treatment agent 58 contacting the barrier 54. According to this version of retention process, the barrier 54 is initially applied to the target location and allowed to bind to the tissue surface. The agent 58 is subsequently contacted with the barrier and post-treatment agent adheres to the barrier. By the agent anchoring to the barrier, the agent is hindered from being transported away and remains at the tissue site for a longer period of time than if the barrier is not present.

Some exemplary post-treatment agents include antithrombotic drugs (such as heparin, prostacyclin, salicylates), blood plasma proteins (such as albumin), thrombolytic agents (such as streptokinase, urokinase, TPA, APSAC), anti-inflammatory agents (such as steriodal and nonsteroidal drugs), combinations thereof, and the like. In still another embodiment, as shown in FIG. 2B, the tissue 70 with barrier 76 with binding member 78 on two opposing surfaces 72 and 74 is both pre-treated and post-treated with agents 80 and 82, respectively. According to this retention process, agent 80 is administered, the barrier 76 is subsequently attached to two surfaces 72 and 74, and then agent 82 is presented. The agents 80 and 82 may be the same type of agent or different types of agents. For example, agent 80 may be an anti-proliferative drug and agent 82 may be an anti-clotting drug, such as heparin.

Methods of Using the Retention System

The barrier and agent are presented to the target site in a time-varied manner, wherein the barrier is provided at a different time from the introduction of the agent. However, it is essential that the agent and barrier both be present at or near the target tissue during at least partially overlapping times. The process may include successive contact of agent with the target site followed by contact with the barrier to the target surface. In another embodiment, first the barrier and then the agent is sequentially introduced. The gap of time between contacting the agent and barrier is typically very short, especially where the dispensing of agent precedes the barrier. A time gap from 5 to 10 minutes is common and more usually 1 to minutes. The time gap is based on clinical factors familiar to one skilled in the art.

In one process, the tissue is pre-treated with a prescribed amount of agent by contacting the agent to the tissue. The agent may be allowed to penetrate the walls of the tissue, whereby the agent is absorbed into the various layers of the tissue wall. However, the agent may also remain at the tissue surface or penetrate through the entire thickness of the tissue wall and reside at the opposite tissue surface.

The amount of agent introduced to the tissue depends on many factors including the measure of the apparent tissue space available to contain the agent, the particular application for the agent, the type of agent used, the mode of delivery of the agent, the medium in which the agent is conveyed to the tissue, etc.

The amount of barrier that is introduced is a sufficient amount to hinder transport of agent from the tissue site, for example a sufficient amount of barrier may hinder diffusion of the agent through the tissue surface. The term "sufficient amount" as used herein, means the minimum amount necessary to cause a particular event, e.g. increased agent retention time. The term "hinder" refers to a slower passage rate compared to the passage rate under the same conditions but without application of the barrier according to the present invention.

The optimal barrier dosage can be determined by monitoring the agent residence time and accordingly varying the amount and timing of barrier administration relative to agent administration. The amount of applied barrier may be ample enough to create a single continuous layer of coating on the entire surface of the tissue. In other embodiments, the barrier amount is adequate for a dispersed spotting of non-continuously attached barrier to the tissue surface. In still other embodiments, multiple layers of barrier are attached to the tissue surface. Multi-layers are useful for prolonging the presence of barrier on the tissue, as compared to single layers or dispersed barrier. The multiple layers allows some barrier to remain on the tissue surface longer because the external layers are degraded first whereas the layers closer to the tissue surface remain for a longer prior of time. Multilayers may be applied where a barrier with a charged binding member has a $pK_a$ value that is different from physiological pH. The underlying layers are protected from environmental pH for a longer period of time.

Barrier amounts influence the rate of agent diffusion and length of time that the barrier effectively hinders the agent before the barrier is degraded. A sufficient amount of barrier will provide agent retention times greater than the retention time in the absence of the barrier. Usually an amount of barrier is provided sufficient to initially hinder at least 75% of agent present in the tissue from being transported away from the tissue site, e.g. diffusing through the tissue surface, and more usually the barrier initially hinders at least 90% of agent transport. After time, the barrier degrades and these percentages decrease. Where a long retention time and slow rate of diffusion is desired, a thicker coating of barrier may be applied. The barrier may be so thick that all agent transport is temporarily blocked.

The amount of barrier to be administered into a patient will vary with the barrier, the agent, delivery vehicle, treatment, etc. The barrier concentration should be related to the barrier binding member's relative affinity for the tissue surface and the concentration of agent used. As the affinity of the barrier for the tissue surface increases, the required concentration of the appropriate barrier will decrease. Optimization of the barrier to provide maximum agent retention should be carrier out using the methods described herein, once the barrier have been decided upon.

The agent and barrier are delivered to the target tissue in a carrier, which may be a liquid, solid, gel or the like. Typically, the agent and barrier are suspended in separate portions of a fluid. The fluid that carries the materials to the tissue is any liquid or gas of interest. Exemplary fluids are water, saline, blood, plasma, etc. In some embodiments, the fluid is useful for creating a particular environment within the tissue, such as modulating pH, temperature, and the like. Thus, the fluid would possess the necessary characteristics to alter the tissue environment. In other embodiments, the fluid is non-reactive with the tissue and may be useful in washing the tissue. The barrier and/or agent are combined with the carrier in the usual manner as is well understood in the art. The barrier is present in the carrier at least in amounts sufficient to provide and increase in agent retention time.

Exemplary retention processes are represented below. As will be apparent to one skilled in the art, the process may be practiced with other instruments and techniques that are per se known.

To set up a retention system, the patient is prepared according to conventional procedures known in the art. Usually the patient is given an anesthesia.

In one embodiment of the retention process, a conduit, e.g. catheter, is inserted at or near the target tissue. For example, where the target site is the aorta as shown in FIG. 3, the retention system 100 includes a catheter 102 that may be percutaneously inserted into the right femoral artery 120 through a cut down 122. In other embodiments, various arteries may be used for entry of the catheter, such as a radial artery, brachiocephalic artery, common carotid artery, or other similar vessels. The catheter 102 having an inflatable balloon 104 is advanced through the descending thoracic aorta to the ascending aorta 124 where agent and barrier 112 in injected. In other embodiments, the delivery catheter is pushed further from the aorta and into a coronary artery, such as the left main coronary artery, left anterior descending artery or right coronary artery. The proximal end of the exemplary catheter in FIG. 3 has an inflation port 106, guide wire port 108 and fluid source opening 110. In other cases, where the target tissue is a coronary vein, the catheter may be percutaneously introduced into the right jugular vein 130 and snaked into the appropriate vein.

Care must be taken while inserting the catheters that the vessels do not dissect or perforate. Furthermore, the inserting vessels must not become obstructed, potentially resulting in conditions including peripheral ischemia, systemic infection, thrombocytopenia, hemorrhage and hemolysis.

The pressure used to deliver the agent and barrier through the catheter should be sufficient to assure contact of the material with the tissue walls and minimize vessel trauma. Pressure amounts depend, inter alia, on catheter pore size and number, length of the catheter, diameter of the delivery lumen and atmospheric pressure. Exemplary moderate pressure amount is between about 2 and 10 ATM, usually about 2 and 5 ATM, and more usually about 4 ATM. Where the tissue is pre-treated with the chemical agent, typically the pressure used to deliver the agent is higher than the pressure used to deliver the barrier. In contrast, where the tissue is post-treated with a chemical agent, usually the pressure for delivery of the barrier is higher than the pressure used to administer the post-treatment agent.

The material may be ejected into the interior of the vessel or organ from the surface or tip of the catheter. The material may be positioned on a balloon, such as a standard angioplasty balloon catheter, microporous balloon catheter, or infusion catheter. In addition, the polymer may be administered by spraying, extruding or otherwise internally delivering the material by a tubular device having multiple lumens.

Successive administration to the patient of agent and then barrier may be chosen. In another embodiment, the barrier and then agent is successively administered. Still, in other embodiments the barrier and agent are administered to the patient at the same time, but the barrier and agent contact the target site at varying time intervals.

Measurement of Agent Residence Time

The relative ability of compounds to act as barriers and to increase agent retention time can be estimated using in vitro and in vivo agent concentration measurements. The increase in retention time of the agent in the tissue attributable to the administration of the barrier may be determined by measuring the total concentration of agent in the tissue over time after introduction of the barrier and after dispensing of only the agent. Where a pre-treatment agent is used, in vivo assays of the amount of agent diffusing across the tissue surface indirectly indicate agent retention time because decrease of diffusion affects agent retention in the tissue over time. Although even a minimally measured increase of retention time is all that is required for a barrier to be useful, most commercially desirable barriers increase retention times by at least 10% and usually by at least 50% and more usually by at least 90% of the difference between retention time in the presence of the barrier and retention time in the absence of the barrier.

One may measure the amount of agent introduced into the tissue and the amount of agent remaining over a course of time after the barrier is applied.

In summary, the various techniques described above for screening candidate barrier compositions by assaying for the agent concentration in the target tissue are all generally useful as methods of identifying compounds that are most useful for increasing agent retention times in a mammalian tissue. In all of these assays, the best barriers are those compounds selected from the candidate of compounds being tested that best inhibit agent transport away from a tissue of the mammal, either by direct testing in vivo or by a test that predicts such transport.

EXAMPLES

1. In-Vitro Increase in Drug Retention in Vascular Vessels by Treatment with a Poly(amine) Barrier Procedure The target tissue is a live excised porcine carotid. The tissue sample is perfused with buffered saline of Kerbs-henseleit Buffer (Sigma Catalog #K3753) at physiological temperature and pressure. Thereafter, the excised vessels are received in buffered saline solution. The artery segments are sutured to tubing using plastic nipple adapters and loaded into a perfusion chamber. The segments are stretched to their original lengths. In the perfusion chamber, the vessels are allowed to equilibrate for 10 minutes at 37° C. the hydrostatic pressure head above the chamber is about 100 cm.

A microporous balloon catheter is inserted through the rotating hemostatic valve (RHV) and secured. The agent used is 0.01% w/v of Poly(amine) Barrier. The agent is delivered through the catheter at 3.5 atm pressure for 2 minutes in both control and test samples. The amount of agent delivered is about 3 ml. Immediately following agent introduction, a barrier of Poly(amine) Barrier is delivered through the catheter in only the test samples for about 2 minutes. The total amount of barrier introduced is about 3 ml.

Results

The test and control vessels are flushed with the buffer solution for about 15 minutes. The proximal and distal positions of the vessels are marked and the vessels are removed from the perfusion chamber and placed into a bath containing liquid nitrogen. The vessels are mounted in paraffin and sliced in 10 micron thin sections at the proximal, mid and distal portions.

FIGS. 4A to 4B show images of proximal, mid and distal sections of the vessel wall exposed to agent. A sample fluorescent image of a control vessel treated with cascade blue alone is depicted in FIG. 4A. The test vessel with cascade blue followed by poly-L-lysine, as illustrated in FIG. 4B, has greater intensity, representing a larger amount of agent retained. Both FIGS. 4A and 4B show the highest intensity is at the luminal intima and decreased intensity along the thickness of the vessel wall.

The slides are observed using a fluorescent microscope. The fluorescent intensities of the sections are recorded, where fluorescence represents the presence of agent in the tissue. The resulting intensities over the length of the tissue sections are represented in the graphs in FIG. 5A showing the proximal section and FIG. 5B showing the mid section. The intensities, as shown in Table 2, indicate that delivery of poly-L-lysine following cascade blue delivery results in a decrease in the release of the dye. The average intensity of agent in the test sample is about 1083, whereas the control intensity is about 749. Thus, a 44% increase in agent occurs with the use of the barrier. By this data, it is apparent that the residence time of the agent in the vessel wall increases with the presence of barrier. The polycation adheres to the vessel wall by ionic binding and restricts the drug from freely diffusing out of the tissue.

TABLE 2

| SECTION | CONTROL (Cascade blue) | TEST (Cascade blue + Poly-L-lysine) |
|---|---|---|
| Proximal | 669 | 921 |
| Mid | 831 | 1191 |
| Distal | 747 | 1138 |
| Average | 749 ± 81 | 1083 ± 143 |

2. Poly(amine) Barrier to Increase Drug Retention in Renal Tissue

The procedure described in Example 1 is performed, where the tissue is renal tissue.

3. Poly(amine) Barrier to Increase Drug Retention in Tumor Cells

The procedure described in Example 1 is performed, where the tissue is tumor cells.

4. In-Vivo Treatment with a Poly(amino acid) Barrier in a Vascular Vessel following PTCA A healthy, domestic swine is prepared for treatment with cascade blue agent and poly-L-lysine barrier. Three days prior to the operation, the animal is administered 500 mg p.o.q.d. ticlopidine and 325 mg q.d. aspirin. The animal is anesthetized with intramuscular administration of 6 mg/kg tiletamine/zolazepam. Salivary and respiratory secretions are controlled by intramuscular administration of 20 ug/kg atropine. Furthermore, relaxation of the jaw is achieved by isoflurane administered with a facemask and the trachea is intubated. An indwelling intravenous catheter is placed in a peripheral ear vein and fluid therapy is maintained to replace lost blood, usually at a rate of 10 ml/kg per hour. Under sterile conditions, a femoral arteriotomy is performed and an 8F introduction sheath is put in place. Heparin at 200 units/kg is administered.

Prior to coronary angiography, 500 ug.i.c. of nitroglycerin is administered. Usually at least two orthogonal views of a coronary angiogram is taken and the images recorded. A 7F guiding catheter with at least 0.035" guide wire is advanced into the ascending aorta to the ostium. The target vessel has a diameter between 3.0 and 3.4 mm and with minimal bifurcation. The target is located by using an intravascular ultrasound. The 0.035" guide wire is pulled out and a 0.014" wire, such as ACS Hi-Torque Balance Middle Weight, is introduced to the target site. A PTCA catheter is advanced to the target site. The site is denuded by inflating the catheter balloon to a diameter of 1.1:1 ratio of balloon to artery and the catheter is withdrawn.

A microporous catheter balloon, such as ACS Rocket RX Catheter (by Guidant Corp. located in Santa Clara, Calif.) is introduced into the denuded site. An inflation device, such as 20/20 Indeflator Inflation Device™ (by Guidant Corp. located in Santa Clara, Calif.) with a 0.1 μm filter is filled with cascade blue agent and attached to the RHV. Agent is administered at 3.5 atm and at a rate of 1.5 ml/min. for 2 minutes. An inflation device, such as 20/20 Indeflator Inflation Device™, is filled with poly-L-lysine barrier and attached to the RHV. Barrier is administered at 3.5 atm and at a rate of 1.5 ml/min. for 2 minutes. The guide wire is pulled back, to allow blood perfusion. The TIMI flow is observed. The catheter is withdrawn. The amounts of agent and barrier administered are determined by measuring the amounts of agent and barrier remaining in the inflation devices.

The increase in agent retention may be observed by sacrificing the animal and removing the heart. The appropriate vessels are dissected and agent amounts are determined according to the process described above in the result section of Example 1. The agent amounts are compared to a control that is administered agent in parallel to the test animal, but without the introduction of barrier.

The present invention has been described above in varied detail by reference to the particular embodiments and figures. However, these specifics should not be construed as limitations on the scope of the invention, but merely as illustrations of some of the presently preferred embodiments. It is to be further understood that other modifications or substitutions may be made to the described information transfer system as well as methods of its use without departing from the broad scope of the invention. Therefore, the scope of the invention should be determined by the following claims and their legal equivalents.

What is claimed is:

1. A method of formulating a biodegradable composition for hindering transport of an agent away from a tissue, the method comprising:

admixing a barrier having a binding member and a delivery carrier, the binding member being present in an amount sufficient to couple to a surface of the tissue and to permit transport of the agent from the tissue at a lower rate than transport in the absence of the binding member, wherein the barrier is biodegradable and hinders transport of the agent away from the tissue, but allows the agent to migrate towards the tissue.

2. The method of claim 1, wherein the binding member is a counter ion of an ionic member on the surface of the tissue for attachment of the binding member.

3. The method of claim 2, wherein the binding member is a cationic member and the member on the surface of the tissue is an anionic member.

4. The method of claim 2, wherein the binding member is an anionic member and the member on the surface of the tissue is a cationic member.

5. The method of claim 1, wherein the barrier component includes an amino acid.

6. The method of claim 5, wherein the amino acid is poly-L-lysine.

7. A biodegradable barrier composition produced by the process of claim 1.

8. A biodegradable fluent barrier for hindering transport of an agent away from a vessel comprising:

an ionic binding member for adhering to a counter ion member on a surface of the vessel;

a delivery carrier admixed with the ionic binding member; and a passive platelet inhibitor, wherein the barrier is separate from the agent, and wherein the barrier hinders transport of the agent away from the vessel, but allows the agent to migrate towards the vessel.

9. The barrier of claim 8, wherein the counter ion is anionic and the binding member is cationic.

10. The barrier of claim 8, wherein the counter ion is cationic and the binding member is anionic.

11. The barrier of claim 8, wherein the barrier includes a naturally occurring amino acid.

12. The barrier of claim 11, wherein the barrier includes a poly(amino acid).

13. The barrier of claim 12, wherein the barrier includes a poly-L-lysine.

14. A retention system for prolonging residence time of an agent at a tissue site, the system comprising:

a biodegradable barrier having a delivery carrier admixed with a binding member for adhering to the surface of the tissue, wherein the barrier is separate from the agent; and a conduit having at least one opening for administering the agent and barrier to the tissue site, wherein the barrier hinders transport of the agent away from the tissue, but allows the agent to migrate towards the tissue.

15. The retention system of claim 14, further including a pump for applying pressure to the conduit.

16. The retention system of claim 14, wherein the binding member is a cationic member and the surface of the tissue includes an anionic member for attachment of the binding member.

17. The retention system of claim 14, wherein the barrier includes an amino acid.

18. The retention system of claim 17, wherein the amino acid is poly-L-lysine.

* * * * *